United States Patent [19]

Potter et al.

[11] Patent Number: 4,672,956

[45] Date of Patent: Jun. 16, 1987

[54] BANDAGES, COMPONENTS THEREOF AND USE

[75] Inventors: William D. Potter, Stortford; Sinan B. Kiamil, Harlow; Nicholas D. White, Stortford, all of United Kingdom

[73] Assignee: Smith and Nephew Associated Companies p.l.c, United Kingdom

[21] Appl. No.: 562,593

[22] PCT Filed: May 6, 1983

[86] PCT No.: PCT/GB83/00133

§ 371 Date: Oct. 19, 1983

§ 102(e) Date: Oct. 19, 1983

[87] PCT Pub. No.: WO83/03973

PCT Pub. Date: Nov. 24, 1983

[30] Foreign Application Priority Data

May 6, 1982 [GB] United Kingdom ............... 8213169
Jul. 23, 1982 [GB] United Kingdom ............... 8221385
Aug. 24, 1982 [GB] United Kingdom ............... 8223254
Dec. 22, 1982 [GB] United Kingdom ............... 8236413

[51] Int. Cl.$^4$ ............................................. A61F 5/04
[52] U.S. Cl. .................................... 128/90; 427/2; 427/389.9; 428/264; 428/265; 428/268; 428/311.5; 428/319.7; 428/255

[58] Field of Search ............ 427/389.9, 2; 128/90, 128/155, 156, 68, 77; 428/264, 265, 268, 311.5, 319.7, 255

[56] References Cited

U.S. PATENT DOCUMENTS

| | | | |
|---|---|---|---|
| 3,630,194 | 12/1971 | Bourdman | 128/90 |
| 3,874,376 | 4/1975 | Dart et al. | 128/90 |
| 3,908,644 | 9/1975 | Neinart et al. | 128/90 |
| 4,052,282 | 10/1977 | Kubushiro | 428/273 |
| 4,214,578 | 7/1980 | Gianakakos et al. | 528/495 |
| 4,286,586 | 9/1981 | Potts | 128/90 |
| 4,316,457 | 2/1982 | Liegeois | 427/389.9 |
| 4,344,423 | 8/1982 | Evans et al. | 128/90 |
| 4,376,438 | 3/1983 | Straube et al. | 427/2 |
| 4,465,713 | 8/1984 | Lock et al. | 427/385.5 |

Primary Examiner—Joseph L. Schofer
Assistant Examiner—J. M. Reddick
Attorney, Agent, or Firm—Jacobs & Jacobs

[57] ABSTRACT

An orthopaedic bandage is described which comprises a support carrying a vinyl compound, which compound polymerizes when exposed to a water-activated vinyl polymerization catalyst, characterized in that the vinyl compound is a hydrophilic prepolymer which contains not less than two polymerizable vinyl groups. Use of a hydrophilic prepolymer which contains not less than two polymerizable vinylic groups results in a storage stable bandage which on exposure to a water activated polymerization catalyst produces a cast of good strength.

19 Claims, No Drawings

BANDAGES, COMPONENTS THEREOF AND USE

The present invention relates to an orthopaedic bandage which hardens as a result of polymerisation of vinylic groups, prepolymers for use in such bandages and to the use of such bandages for immobilising parts of the body and to splints formed therefrom.

Traditionally, Plaster of Paris has been used in orthopaedic bandages or splinting bandages. However, in recent yeaars there has been a tendency to seek lighter materials. One approach to providing such orthopaedic bandages has been to employ isocyanate containing compounds which polymerise on exposure to water and in doing so harden and set. Bandages of this kind are described in DT No. 2651089, GB No. 1578895, EPO No. 0057988 and PCT WO 81/00671. However isocyanates are highly reactive towards moisture and require complicated manufacturing and storage processes to prevent premature setting. An alternative approach to provide a lightweight synthetic splinting agent is to employ material which can polymerise on exposure to ultra violet light. Such systems are disclosed on GB No. 1407795, GB No. 1512553, U.S. Pat. No. 3,881,473 and U.S. Pat. No. 3,985,128 but such systems have not proved entirely satisfactory and require a light source which is not always convenient. A third approach which avoids the water sensitivity of the isocyanate system and does not require the light source of the ultra violet activatable system employs solid, water-soluble vinylic monomers which can be caused to polymerise and, in so doing, to harden and set. Bandages of this kind which employ vinylic polymerisation are described in GB No. 1592228, GB No. 2021128A, EP No. 008195, U.S. Pat. No. 3,630,194, U.S. Pat. No. 3,968,791, U.S. Pat. No. 4,134,397 and U.S. Pat. No. 4,214,578. Such bandages comprise a support carrying a cast-forming composition comprising a solid, water-soluble vinyl monomer which polymerises when exposed to a water-activated vinyl polymerisation catalyst, thereby causing the cast to set, some require disadvantageously elevated temperatures to cause setting. A related system is described in U.S. Pat. No. 3,908,644 but that required somewhat hazardous solvents to be employed for the catalyst system described. These various known vinylic orthopaedic bandages can suffer from problems pertaining to low strength, shelf life, difficulties in their application due to their being brittle, emloying crystalline solids or volatile liquids, and the like. It has now been found that by avoiding the necessity of using such monomers it is possible to provide bandages which have an acceptable shelf life and which do not suffer from other problems associated with the use of known bandages.

Clearly there is a need for a synthetic splinting system which can be employed without recourse to highly water sensitive materials such as polyurethane being present in the bandage, which does not require a light source to activate the system, which does not employ toxic solvents in order to activate the system, which can be activated at room temperature, which can produce a strong cast and which does not require complicated packaging.

In one aspect, the present invention provides an orthopaedic bandage which comprises a support carrying a vinyl compound, which compound polymerises when exposed to a water-activated vinyl polymerisation catalyst characterised in that the vinyl compound is a hydrophilic prepolymer which contains not less than two polymerisable vinylic groups.

It has been discovered that by using hydrophilic prepolymer which contains not less than two polymerisable vinylic groups that a storage stable, readily activatable bandage can be produced which on exposure to a water activated polymerisation catalyst produces a cast of good strength.

The water activated vinyl polymerisation catalyst used in the bandage will usually comprise more than one component. It is believed that the most effective catalyst for use in the bandages of this invention will be a redox catalyst which will comprise an oxidising component and a reducing component. If desired neither of these components need be in association with the prepolymer prior to introducing water to the system as they may be introduced in solution. However, for the sake of convenience it is preferred that at least one component is in association with the prepolymer prior to introducing water to the system and it is much preferred that the catalyst (that is all components of the catalyst) are in association with the prepolymer prior to introducing water to the system. It is one of the very considerable advantages of the preferred bandages of this invention that the catalyst is in association with the prepolymer so that the bandage need only be introduced to water (rather than a solution of the catalyst or a component thereof) in order to make it set. Use of a hydrophilic prepolymer having not less than two polymerisable vinyl groups, and especially one which is a viscous liquid, has been found to allow the preparation of a storage stable bandage which can include the catalyst ab initio so that introduction of water is sufficient to cause the bandage to set.

Prepolymer is used herein in its conventional sense to mean an oligomer (that is a material intermediate between the monomer or monomers and the final polymer; as is understood in the polymer art such materials are of relatively low molecular weight compared to the final polymer but exclude monomers).

Preferred prepolymers are viscous liquids since bandages employing such materials have been found to have better unrolling and setting properties than those employing solid materials (especially after storage).

The prepolymer for use in orthopaedic bandages of this invention is most suitably a low molecular weight material which is capable of being polymerised further. Suitble low molecular weights include number average molecular weights in the range 400 to 24,000, preferably 600 to 20,000, in particular 1,100 to 16,000.

The prepolymer must, of course, be one which is sufficiently attractive to water to be itself capable of polymerising (causing the cast to set) when exposed to a vinyl polymerisation catalyst which is activated by introduction of water and, therefore, in this sense the prepolymer is a hydrophilic prepolymer. Hydrophilic prepolymers have proved surprisingly advantageous in producing a bandage which wets through uniformly and produces a good quality cast.

Normally the hydrophilic prepolymer employed will be one which swells on addition of water (that is if the dry prepolymer is exposed to water it takes up water but does not dissolve therein). It has been found that such hydrophilic prepolymers give a rapid setting time to the bandage and also have been found to give improved cast strength to the set bandage. Preferred hydrophilic prepolymers are capable of absorbing at least 5% and more aptly at least 10% by weight of their own weight of water. A simple method of determining how much a prepolymer swells on addition of water is to determine the increase in weight of a thin film (eg 25 microns) of dry prepolymer supported on a glass slide when introduced to an atmosphere saturated in moisture vapour until equilibrium is reached. It has been found to be particularly advantageous to employ a hydrophilic prepolymer which is dispersible in water (that is infinitely mixable with water but does not dissolve).

The prepolymer contains not less than two vinyl groups per molecule, (average functionality when, as is normal, the prepolymer is a mixture of compounds) and preferably the prepolymer contains not less than 3 vinyl groups per molecule. It has been found that particularly good cast strength can be achieved by employing hydrophilic prepolymers containing not less than 3 vinylic groups per molecule. Generally the prepolymer contains not more than 6 vinyl groups per molecule and suitably contains not more than 4 vinyl groups per molecule. The preferred prepolymer employed in this invention contains 3 vinyl groups (average functionality).

Normally the vinylic group will be in a terminal or pendant position of the prepolymer molecule as this has been found to allow ready polymerisation of the prepolymer.

Favourably the vinyl group is selected from an acrylic or methacrylic group. Thus, from the foregoing, it will be appreciated that highly favoured bandages of this invention comprise a hydrophilic prepolymer having not less than 2 acrylate or methacrylate groups per molecule in association with which is a water activatable acrylic polymerisation catalyst. Although acrylate or methacrylate esters are preferred, analogous amides are also apt. Preferably the vinyl group is an acrylate or methacrylate ester group and more preferably the vinyl group is a methacrylate ester group.

From the foregoing it is clear that favoured bandages of this invention will utilize a hydrophilic prepolymer which contains not less than 2 and preferably not less than 3 acrylate or methacrylate groups. Preferred prepolymers for use in the bandage of this invention contain 3 acrylic or methacrylic ester groups per molecule.

We have found, as discussed further hereinafter, that inclusion within the hydrophilic prepolymer employed in the bandage of this invention of a tertiary amino group has considerable surprising advantages. Thus, for example, use of a prepolymer containing a tertiary amino group aids in producing a bandage with favourable storage stability (for example a stable level of tack prior to introduction of water) and favourable setting time. Bandages employing prepolymers of the type hereinbefore described which also contain a tertiary amino form an especially favoured aspect of this invention. The most apt tertiary amino groups for inclusion in the molecule are pendant diloweralkylaminoloweralkyl groups (in which lower alkyl has up to six carbon atoms and more suitably up to 3 carbon atoms) of which dimethylaminoloweralkyl groups are most suitable and of which the dimethylaminoethyl group is preferred. Such amino groups may be incorporated into the prepolymer by having employed an appropriate alkanol, for example dimethylaminoethanol, as precursor.

We have also found, as discussed further hereinafter, that inclusion of polyethylene oxide residues (for example 6 to 40% by weight) aids in producing prepolymers which are particularly suitable for use in the bandages of this invention.

Additionally we have found, as discussed further hereinafter, that the favoured prepolymers for use in the bandages of this invention employ vinylic groups derived from acryloyloxyloweralkoxy or methacryloyloxyloweralkoxy groups of which the methacryloyloxyethyloxy group is preferred.

Also, as described hereinafter, the bandage of this invention most suitably employs a prepolymer derived from an aliphatic isocyanate having an isocyanate functionality of not less than 2 and preferably an isocyanate functionality of 3.

The prepolymers employed in this invention are normally prepared by the condensation of smaller molecules which containing mutually reactive functional groups, for example alcohols or amines may be condensed with isocyanates or acid halides. In order to ensure that the prepolymer has the desired number of vinyl groups it is normal that at least one of the condensing molecules is polyfunctional, for example a polyisocyanate may be condensed with a vinyl compound which is suitably functionalised, for example with a hydroxy group so that it is an alcohol, or alternatively a polyol may be reacted with a vinyl compound which is suitably functionalised, for example in the form of an acid chloride or which is functionalised in a way which provides it with an isocyanate group. We prefer to prepare prepolymers for use in this invention by condensing an isocyanate containing molecule with a hydroxyl containing molecule and we have found it most convenient to employ the hydroxyl containing molecule as the source of the vinylic group. However, as will be apparent hereinafter, considerable latitude is allowed the skilled worker in selecting the components to bring together to form the prepolymer with the desired properties.

The prepolymer used in this invention will be hydrophilic. The hydrophilic property is most aptly obtained by including within the prepolymer groups which will increase its attractiveness to water. Suitable groups for this purpose include polyoxyalkylene groups, salted amino groups, hydroxyl groups and salted carboxyl groups. The group we find most suitable for inclusion in the molecule are polyoxyalkylene groups, particularly those containing high proportions of polyoxyethylene residues such as those derived from polyethylene glycol. The use of sch moieties is considered furthere hereinafter.

The prepolymers employed in this invention can have the hydrophilic groups included within its structure by condensing together several species in one reaction (for example a polyisocyanate may be reacted with a polyethylene glycol and a vinyl compound containing a hydroxyl group in the same reaction) or the hydrophilic groups can already be present in one of the species (for example a polyisocyanate may be reacted with a vinyl compound which contains hydrophilic moieties, for example one in which polyethylene glycol has been condensed onto a hydroxyl group of the vinyl compound). Various apt ways of ensuring the presence of the required hydrophilic groups are described hereinafter.

As previously indicated, the hydrophilic prepolymer can be one derived from the reaction between a suitably functionalised vinyl group containing compound and an organic compound having a functionality of not less than 2. It will be appreciated that references therein to numbers of groups per molecule and functionality relate to average numbers and functionalities.

'Suitably functionalised' of course means that the vinyl group containing compound contains a groups suitable for reaction with the polyfunctional organic compound.

The hydrophilic nature of the prepolymer may be conferred, at least in part, by hydrophilic groups originally present or derived from the vinyl group containing compound.

In general, the more hydrophilic groups in the prepolymer molecule, the more hydrophilic the prepolymer will be. Suitable hydrophilic groups containing vinyl compounds include ethylene oxide adducts. Such compounds can have from 1 to 20 oxyethylene groups per molecule and preferably from 1 to 10 oxyethylene groups per molecule. Suitable hydrophilic groups containing vinyl compounds of this type include the acrylate and methacrylate esters of ethylene glycol and polyethylene glycol.

An apt hydrophilic group containing vinyl compound is a polyethylene glycol monomethacrylate with an average of five oxyethylene groups per molecule and an average molecular weight of from 300 to 400. A compound of this type is known as Sipomer PEG MM made by Alcolac Chemicals Inc. Sipomer PEG MM has an average molecular weight of about 364. Another compound is known as PE 350 made by Kanematsu Goshu and available from R. W. Unwin.

The terminal hydroxyl groups provide suitable functionalisation for reaction with a polyfunctional organic compound (such as a polyisocyanate which is reactive towards hydroxyl groups). This is further discussed hereinafter.

However it is not necessary for the vinylic component to contain hydrophilic groups since these may be derived from the other precursor of the prepolymer.

Preferred bandages of the present invention use a prepolymer derived from a suitably functionalised vinyl group containing compound, a suitably functionalised hydrophilic group containing compound and an organic compound having a functionality of more than one capable of reacting with the aforementioned compounds.

The resulant prepolymer thus has a vinylic component, a hydrophilic component and a linking component. (derived from the organic compound).

Such polymers are preferred since separation of the vinyl group and the hydrophilic group or groups into two different components generally results in a harder setting prepolymer than one containing a hydrophilic vinyl component.

Suitable vinylic components include those containing acrylic and methacrylic groups, as described hereinbefore. Favourably such vinylic components are derived from suitably functionalised acrylamides and methacrylamides and preferably from acrylate and methacrylate esters. Preferred vinylic components include those derived from suitably functionalised alkyl esters of acrylic and methacrylic acid.

Suitable functionalising groups include hydroxyl and amino where the formative reaction is with a polyfunctional organic compound which is reactive towards hydroxyl and amino groups. This is further discussed hereinafter. The preferred functionality group is the hydroxyl group.

Favoured vinylic components thus include those of the general formula:

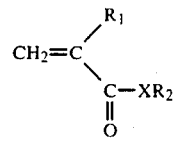

wherein $R_1$ is a hydrogen or methyl; X is O or NH and $R_2$ is a group which will be O- or N-substituted in the prepolymer and selected from; hydroxyalkyl, hydroxyaryl, aminoaryl and aminoalkyl and aminoaryl optionally substituted at the nitrogen by an alkyl. Apt alkyl groups contain not more than 6 carbon atoms. Favoured alkyl groups contain 2 or 3 carbon atoms.

Favoured functionalised vinyl compounds include hydroxyethyl esters so that particularly favoured vinylic components include acryloyloxy-ethoxy and methacryloyloxy-ethoxy groups.

A preferred compound is 2-hydroxyethyl methacrylate, so that preferred vinylic components include the methacryloyloxyethoxy group. Generally when employed this component comprises 6 to 45% wt/wt of the prepolymer, more usually 16 to 40% wt/wt of the prepolymer and preferably 17 to 34% of the prepolymer. Analogous vinylic components will generally be employed on an equivalent wt/wt basis.

The hydrophilic component is preferably a polyalkylene oxide such as polyethylene oxide or a polyethylene oxide containing polymer. These may be homo- or co-(including block co-)-polymers of polyethylene oxide and other alkylene oxides such as propylene oxide.

Suitable examples of the hydrophilic component include derivatives of polyalkylene glycols and polyalkoxylated mono- and poly-ols and polyalkoxylated mono- and poly-amines, in particular such compounds based on homo- or co-(including block co-)polymers of ethylene oxide or propylene oxide. Hydrophilic components derived from polyethylene glycols or polyethylene glycol monoethers are preferred of which those derived from polyethylene glycols are particularly preferred.

The hydrophilic compound suitably may have a functionality of 1 to 5, favourably 2 to 3 and preferably 2.

The ethylene oxide content of the hydrophilic component is desirably at least 50% by weight and preferably at least 80% by weight of the hydrophilic component.

The hydrophilic compound is preferably dispersible in water.

Favoured examples of the hydrophilic compound include polyalkylene glycols and glycol monoethers, in particular such glycols and ethers based on homo- or co- (including block co-) -polymers of ethylene oxide and propylene oxide. Polyethylene glycols and glycol monoethers are preferred and polyethylene glycols are particularly preferred.

Favoured hydrophilic components thus include those of the general formula:

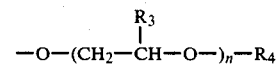

wherein n is 10 to 225; $R_3$ is hydrogen or methyl, $R_4$ is a bond, hydrogen or lower alkyl; and $R_3$ may be the same or different in adjacent repeat units with the proviso that in at least 50% and preferably in at least 80% of units $R_3$ is hydrogen.

The value of n referred to herein is of course a number average value for the hydrophilic compound and its corresponding component in the prepolymer.

n is most suitably 20 to 140 and is preferably 30 to 40.

Most desirably in all units $R_3$ is hydrogen since, as stated hereinbefore polyethylene oxide based hydrophilic components are preferred.

Suitable polyethylene oxide and/or polypropylene oxide based hydrophilic compounds include polyethylene glycols, for example PEG 400 to PEG 6000, polyethylene glycol-polypropylene glycol block copolymers, for example PL 64 available from Pluronics and polyglycol 78W2800 available from British Petroleum, polyethoxylated mono-ols such as polyethylene glycol monomethyl ether, ethoxylated polyols such as ethyoxylated glycerol, for example as PEG 1256 available from Imperial Chemical Industries Ltd and ethoxylated trimethylolpropanes available from Eugene Kuhlman and ethoxylated amines such as Crodamets and Dicrodamets available from Croda Chemicals Limited. PEG 1500 is particularly suitable for example as available from British Petroleum (Hythe Chemicals Ltd.).

Polyethylene glycols and the prepolymers derived from them are preferred.

The hydrophilic properties of such prepolymers will often depend on the amount and type of the polyethylene glycol from which the prepolymer is derived. The water sensitivity of the prepolymer will usually be proportional to the number of oxyethylene groups in the polyethylene glycol. Thus it is possible to obtain prepolymers with differing hydrophilic properties by varying the proportion and type of the polyethylene glycol used to form the prepolymer.

The hydrophilicity of prepolymers used in the invention is important for a number of reasons. For example it is a factor in determining the rate of the polymerisation of the prepolymer in the presence of the water-activated vinyl polymerisation catalyst. The more hydrophilic groups present in the prepolymer, the more effective the catalyst has been found to be subject to any contrary effect such as the introduction of crystallinity caused by using a polyethylene oxide of high molecular weight.

For this reason it is preferred that the hydrophilic prepolymers of this invention are hydrophilic to the extent that they are water-swellable and capable of absorbing at least 5% w/w and preferably at least 10% w/w of water, as stated hereinbefore.

Other physical properties, such as physical form, also depend to some extent on the percentage amount of the component derived from polyethylene glycol in the prepolymer and the type of glycol used.

The physical form of the prepolymer is also a factor in determining efficiency of catalyst activation where a water-activated catalyst is used, the efficiency of catalysis where a catalyst is used and the rate of polymerisation of the prepolymer. Ease of application and adhesion to the bandage support, and self-adhesion and interlayer polymerisation to form a cast or splint discussed hereinafter have been found to be largely determined by the physical form of the polymer.

For these reasons, it is preferred that the prepolymer is a viscous liquid.

Favoured prepolymers may be obtained by optimisation of the type of glycol used and the proportion of the corresponding component in the prepolymer.

For such prepolymers, apt polyethylene oxide derivatives include the polyethylene glycols having a molecular weight of between 400 and 6000, and favourably of between 600 and 6000. The preferred polyethylene oxide containing compound is a polyethylene glycol having a molecular weight of 1500.

The polyethylene oxide component of the prepolymer is favourably 6 to 40% by weight, preferably 10 to 30% by weight of the prepolymer.

Compared with prepolymers containing a hydrophilic, e.g. ethoxylated vinyl component, prepolymers of the foregoing type are preferred since separation of the vinyl group and the polyethylene oxide into two different components results in a prepolymer which sets harder than if the two moieties are in the same component.

Although the discussion of prepolymer optimisation above has been in terms of optimisation of the type and proportion of polyethylene glycol, similar considerations apply to other hydrophilic compounds furnishing hydrophilic components in the prepolymer.

Thus for example polyoxyethylene-polyoxypropylene diol block copolymers are also apt but less preferred. Suitable polyoxyethylene-polyoxypropylene block copolymers have a molecular weight of between 1500 and 3000 and a polyoxyethylene content of 40 to 60%.

Terminal hydroxyl or amino groups in the hydrophilic compound provide suitable functionalisation for reaction with a polyfunctional organic compound which is reactive towards hydroxyl or amine groups.

The prepolymer contains linkages which will be stable during a vinyl polymerisation reaction. Suitable linkages include ester, ether and amide linkages. Preferably, the prepolymer contains urethane linkages. Such prepolymers containing urethane linkages can be derived from the reaction between an organic isocyanate having a functionality of not less than two and a suitable functionalised vinyl compound (as described above). Such prepolymers may also be derived from a hydrophilic group containing compound (as described above).

Suitable organic isocyanates include aliphatic (including alicyclic) isocyanates and aromatic isocyanates having a functionality of not less than 2. Most suitably the isocyanate has a functionality of not less than 3 and preferably 3. Generally the isocyanate has a functionality of not more than 6 and more usually not more than 5. Preferred isocyanates have been found to be aliphatic isocyanates. Thus aliphatic isocyanates having 3 isocyanate groups per molecule are particularly suitable.

Suitable aromatic and aliphatic isocyanates include any of those generally known in polyurethane chemistry, for example as described in 'Polyurethanes: Chemistry and Technology Part 1 Chemistry' Interscience Publishers (1962) or Kirk-Othmer Encyclopedia of Chemical Technology, 3rd. Ed., John Wiley & Sons, 1981, Vol. 13, p. 789–818.

An apt alicyclic isocyanate which has a functionality of 2 is 1,1'methylene-bis(4-isocyanate-cyclohexane) which is known as Desmodur W (available from Bayer (UK) Ltd.).

Apt aromatic isocyanates include 1,1',1''-methylidyne tris(4-isocyanato-phenyl) which is known as Desmodur R and Desmodur L both having a functionality of 3 and which are available from Bayer (UK) Ltd.

Preferably organic isocyanates are aliphatic isocyanates. A suitable aliphatic isocyanate is a polyfunctional isocyanate derived from hexamethylene diisocyanate having a functionality of three. A favoured aliphatic isocyanate of this type is known as Desmodur N 100 available from Bayer (UK) Limited, Generally the isocyanate accounts for 10 to 60% wt of the prepolymer, more suitably 15 to 55% wt of the prepolymer and preferably 30 to 50% wt. of the prepolymer.

Apt prepolymers for use in orthopaedic bandages of this invention are derived from the reaction between an aliphatic isocyanate having a functionality of not less than two and a mixture of the monomethacrylate (or monoacrylate) esters of ethylene glycol and polyethylene glycol.

Other preferred prepolymers are derived from the reaction between an aliphatic isocyanate having a functionality of not less than two, an acrylate or methacrylate containing compound and polyethylene glycol.

A favoured prepolymer is derived from the reaction between an aliphatic isocyanate having a functionality of three, for example Desmodur N 100, 2-hydroxyethyl methacrylate and a polyethylene glycol monomethacrylate having an average of five oxyethylene groups per molecule, for example PE 350 or Sipomer PEG MM.

A more favoured prepolymer is derived from the reaction between an aliphatic isocyanate having a functionality of three, for example Desmodur N 100, 2-hydroxyethyl methacrylate and a polyethylene glycol such as PEG 6000, or yet more favourably PEG 1500.

It is preferred, in order to avoid any potential problems of toxicity, that the prepolymers used in the present invention are essentially free of monomer. It is one of the considerable advantages of the bandages of this invention that they do not require the presence of a monomeric vinyl compound with the potential toxicity problems connected therewith.

It has also been found that prepolymers derived from the reaction between at least a linking compound having a functionality of more than one, a suitably functionalised vinyl group containing compound, a hydrophilic group containing compound and a suitably functionalised accelerator are particularly useful in bandages of this invention.

An accelerator, in this context, is a substance which increases the setting rate of the orthopaedic bandage. Preferred accelerators are tertiary amines such as N,N-dimethylethanolamine.

Functionalised accelerators may be represented by the general formula:

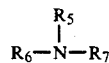

wherein $R_5$, $R_6$ and $R_7$ are each independently a hydrocarbyl radical or any two together are a hydrocarbadinyl diradical, and all three together contain at least one hydroxyl or NH $R_8$ group where $R_8$ is hydrogen or a hydrocarbyl radical.

$R_4$ and $R_8$ may be further substituted by any substituent compatible with the function of the compound.

Each or $R_4$ to $R_8$ may be an alkyl, cycloalkyl or aryl radical or a monovalent radical comprising alkyl, cycloalkyl or aryl components, for example aralkyl; or any two of $R_4$, $R_5$ and $R_6$ together may be polymethylene.

Thus each may be a straight chain alkyl group, preferably $C_{1-4}$ alkyl, $C_{5-8}$ cycloalkyl or phenyl; or any two as above together may be $C_{4-5}$ polymethylene.

Preferably $R_4$ is a hydroxy $C_{1-4}$ alkyl in particular 2-hydroxyethyl. Preferably $R_5$ is methyl. Preferably $R_6$ is methyl.

Most aptly The amine is included in the range $1\times10^{-5}$ to $1\times10^{-3}$ moles $Ng^{-1}$, more aptly $3\times10^{-5}$ to $6\times10^{-4}$ moles $Ng^{-1}$ and preferably $7\times10^{-5}$ to $4\times10^{-4}$ moles $Ng^{-1}$.

Thus in a further aspect, the present invention provides a prepolymer which is substantially free from unreacted isocyanate characterised in that the prepolymer is derived from the reaction between an isocyanate having an isocyanate functionality of not less than two, a suitably functionalised vinyl group containing compound and a suitably functionalised accelerator and optionally a suitably functionalised hydrophilic group containing compound. Most aptly the accelerator is a tertiary amine.

Most aptly the hydrophilic group containing compound is present and contains polyethylene oxide residues.

In a preferred aspect the invention provides a prepolymer of this type characterised in that the vinyl group containing compound is a suitably functionalised acrylic or methacrylic ester or amide, the hydrophilic groups containing compound is a polyethylene glycol and the accelerator is a suitably functionalised tertiary amine.

Preferred novel prepolymers include those novel prepolymers described herein with respect to their use in the orthopaedic bandages of this invention.

The prepolymer when exposed to a water-activatable vinyl polymerisation catalyst and water will polymerise to form a hard material, that is it will set.

Therefore the present invention in a still further aspect provides a novel cast-forming, water curable composition comprising a water-activatable vinyl polymerisation catalyst in association with a polymerisable vinyl compound characterised in that the vinyl compound is a hydrophilic prepolymer which contains not less than two polymerisable vinyl group. (Favoured prepolymers are hereinbefore described.

Preferably, the water-curable composition comprises a water-activatable vinyl polymerisation catalyst and a vinyl prepolymer which is derived from the reaction between an aliphatic isocyanate having a functionality of more than one and an acrylic or methacrylate ester of ethylene glycol and a polyethylene glycol.

Particularly preferably the composition is also derived from a suitably functionalised accelerator of which dimethylethanolamine is most apt.

The composition may alternatively contain at least one component of a multi-component water-activatable vinyl polymerisation catalyst in place of the total catalyst.

Suitable vinyl polymerisation catalysts of this type are well known in the literature.

Preferred water-activatable vinyl polymerisation catalysts are redox polymerisation catalysts. Such catalysts usually comprise two components: an oxidising agent and a reducing agent.

The present invention also provides an orthopaedic bandage comprising a support carrying a vinyl compound which compound polymerises when exposed to a water-activated vinyl polymerisation catalyst characterised in that the vinyl compound is a prepolymer which contains more than one polymerisable vinyl group and said prepolymer is in association with at least one component of a water-activatable vinyl polymerisation catalyst.

As is clear from the description hereinafter of the water-activatable catalyst used in the present invention, 'in association' includes the circumstances where the catalyst or its component(s) where appropriate, may be uniformly dispersed in the prepolymer or impregnated into the support. Preferably the catalyst is mixed in with the prepolymer thereby forming a uniform dispersion.

As is also clear from this description the invention thus also provides an orthopaedic bandage of the type hereinbefore defined, characterised in that said prepolymer is in association with a water-activatable polymerisation catalyst. The catalyst will preferably be uniformly dispersed in the prepolymer.

Where the catalyst is a redox catalyst, the prepolymer is in association with the oxidising agent or reducing agent or, preferably, both.

Suitable oxidising agents include ammonium persulphate, potassium or sodium persulphate, hydrogen peroxide, ferric chloride and copper salts.

Preferred redox polymerisation catalysts include a promoter such as a copper (II) salt. Suitable copper salts can include readily water-soluble salts such as hydrated copper sulphate ($CuSo_4.5H_2O$). The number of copper ions and therefore the rate of the polymerisation of prepolymer will depend to some extent on the amount present in the prepolymer and the water solubility of the copper salt. To obtain a polymerisation rate suitable for setting orthopaedic bandages it is preferred that the copper salt has an adequate (slight) solubility in water. A preferred copper salt of this type is cupric acetylacetonate also referred to as copper (II) acetylacetonate. Copper (II) salts are favoured since they can acto as oxidizing agents.

Suitable reducing agents include ferrous sulphate, sodium sulphite, sodium dithionite, sodium thiosulphate, ferrous chloride, sodium formaldehyde sulphoxylate, sodium metabisulphite and the like. Soluble metabisulphite salts such as the sodium or potassium or ammonium salts are preferred reducing agents of which the sodium salt is most preferred.

A preferred redox polymerisation catalyst comprises a mixture of cupric acetylacetonate and sodium metabisulphite. The ratio of sodium metabisulphite to cupric acetylacetonate in the catalyst mixture can be suitable from 1000 to 1, more usually from 250 to 1, for example 200 to 1 or 50 to 1.

The amount of catalyst used in the polymerisation process, e.g., in association with the prepolymer, is suitably 0.1% to 10% by weight and preferably 0.2 to approximately 3%, e.g. 0.2 to 2% by weight of the prepolymer.

It has been found to be advantageous that where a cast is required which is white in colour, that addition to the resin prepolymer of an amount of an organic polyacid or a salt thereof provides a white cast with better surface characteristics. Favoured organic polyacids include those containing 2 or 3 carboxyl groups and 1, 2 or 3 hydroxyl groups. Particularly favoured organic polyacids include tartaric acid and citric acid and salts thereof which will not interfere with the polymerisation of the prepolymer. The amount of acid used will vary depending upon the acid used. For tartaric acid the amount used is suitably from 0.01 to 1 g and preferably 0.05 to 0.5 g, for example 0.1 g, for each 50 g of prepolymer. For citric acid the amount used is suitably from 0.5 to 5 g and preferably 1 to 2 g, for each 50 g of prepolymer. Tartaric acid and its salts are particularly preferred. Salts may be employed but generally it is more effective to employ the acid. Bandages employing such acids form a favoured aspect of this invention.

Desirably, in orthopaedic bandages of the present invention, the prepolymer is in association with a polymerisation inhibitor to prevent premature polymerisation of the prepolymer during its preparation and storage.

Suitable polymerisation inhibitors include vinyl polymerisation inhibitors of the art. A favoured inhibitor for preventing polymerisation of prepolymers used in bandages of the present invention during their preparation and storage is phenothiazine. A favoured inhibitor for preventing premature polymerisation of such prepolymers during storage is methoxyhydroquinone.

The amount of polymerisation inhibitor in association with the prepolymer can suitably be 50 to 1000 ppm and preferably be 100 to 700 ppm of the prepolymer.

If desired, in orthopaedic bandages of the present invention, the prepolymer is in association with a plasticiser which enables the bandage to be more easily manipulated before it has set. A suitable plasticiser is silicone oil which may comprise approximately 10% w/w of the bandage.

Prepolymers for use in orthopaedic bandages of the present invention may be prepared by reacting a linking compound having a functionality of more than one with a suitable functionalised vinyl group containing compound.

Clearly, 'suitably functionalised' where used herein means that the compound must contain a functional group which will react with the linking compound.

The present invention favourably provides a method for the preparation of novel prepolymers defined above characterised in that an organic isocyanate having a functionality of more than one is reacted with a polyalkylene glycol, a suitably functionalised vinyl group containing compound and a suitably functionalised accelerator so that the polymer so produces is substantially free from unreacted isocyanate.

The reaction may take place by simply mixing the reaction components (i.e. the organic isocyanate and the vinyl group containing compound and, where appropriate, the accelerator and, where appropriate, the separate hydroxy group containing compound). A catalyst such as dibutyl tin dilaurate can then be added to the mixture to increase the rate of reaction (i.e. to speed up the formation of the prepolymer) and the reaction allowed to continue until the exotherm has subsided.

A polymerisation inhibitor as described above may also be added into the reaction mixture during the preparation of the prepolymer. Alternatively, the polymerisation inhibitor can be added to the prepolymer mixture prior to coating it on the support. Either way, the prepolymer is in association with the polymerisation inhibitor.

A plasticiser as described above may also be added into the reaction mixture during the preparation of the prepolymer. Alternatively, the plasticiser can be added to the prepolymer mixture prior to coating it on to the support.

Preferably the reaction takes place in a solvent such as dichloromethane, tetrahydrofuran and mixtures thereof and the like. The preferred solvent is dichloromethane. This is more convenient than reacting the reaction components together in the absence of a solvent and subsequently diluting the prepolymer with solvent.

The prepolymer may then be brought into association with one or more components of a vinyl polymerisation catalyst.

Preferably, the catalyst is in a finely divided state, for example a powder, and is uniformly dispersed or dissolved into the prepolymer. The catalyst may alternatively be impregnated into the support before coating with the prepolymer. More preferably the copper acetylacetonate is employed in a solution (in e.g. dichloromethane) which is mixed into the prepolymer.

A polymerisation inhibitor to prevent premature polymerisation of the prepolymer during storage may also be mixed in with the prepolymer.

Similarly, the prepolymer may be brought into association with a plasticiser by mixing.

Other inert materials may be incorporated into the prepolymer mixture. These material include powdered fillers such as alumina, sodium aluminium silicates (such as Zeolex, available from Zeofin), china clay, powdered molecular seive, aluminium silicate, talc, plaster of paris, calcium phosphate, calcium carbonate, ground glass, silicas and titanium dioxide and fibrous fillers, for example glass fibres and colouring agents. A suitable filler such as alumina may be employed to aid in the mass taking up water. Such alumina filler is G 5438, available from Ransden Limited.

The prepolymer mixture (i.e. the prepolymer and any associated ingredients) shall be sufficiently fluid without requiring modification to be used in the orthopaedic bandages of this invention. One of the advantages of employing a viscous liquid prepolymer is that this desirable end is readily achieved. However solvent dispersions and hot melts can be used if desirable.

The orthopaedic bandage of the present invention comprises a vinyl group containing prepolymer as described above carried on a support. The support will normally be a flexible fabric. The flexible fabric will preferably have apertures of sufficient size to enable water to permeate the bandage and cause it to set. Suitable aperture sizes are 0.2 mm to 10 mm and preferably 0.5 mm to 5.0 mm (minimum dimension of aperture).

Suitable flexible fabrics can be woven, knitted or non-woven fabrics made of materials which are inert to the prepolymer. The support will generally be elongate, and favoured flexible fabric supports are those having a low lengthwise stretch and a high widthwise stretch as such properties give good conformability. A suitable low lengthwise stretch is less than 15%, preferably less than 10%, and in particular less than 5%. A suitable high widthwise stretch is greater than 20%, preferably greater than 50%, and in particular greater than 100%.

To achieve such stretch values, a favoured flexible fabric is a Raschel warp knitted fabric.

Suitable support materials include fibres or filaments of cellulose, polyester, polyamides, polyolefines and glass or mixtures thereof.

Suitable glass fibre fabrics are disclosed in, for example, U.S. Pat. Nos. 4134397, 3985128, 3882857, 3881673, 3793686, 3787272, 3686725, German Offenlegungsschrift No. 2651089 and British Pat. Nos. 1512553 and 1407795

Favoured flexible fabric carriers include gauzes such as leno gauze and warp knitted polyester fabrics. A preferred warp knitted polyester fabric has between 4 to 400 apertures per square centimeter.

Suitable fabric weights for a given thickness depend on the fabric material, but in general suitable weights are in the range 50 to 300 gsm, preferably 100 to 200 gsm.

In another aspect, the present invention further provides a method for the preparation of an orthopaedic bandage which comprises coating or impregnating a support with a vinyl compound which compound polymerises when exposed to a water-activated polymerisation catalyst, characterised in that the vinyl compound is a prepolymer which contains not less than two polymerisable vinyl groups.

Any suitable coating means can be used to coat the flexible fabric including fixed doctor blade over flat bed, or roller and roller coating systems.

It is desirable that the prepolymer mixture during coating is protected from excessive moisture vapour. Suitable coating systems can be enclosed and can be conducted in an atmosphere free from excessive moisture vapour such as dry air, or inert gases for example carbon dioxide or nitrogen. However this is not normally necessary except in highly wet atmospheres since it is one of the considerable advantages of this invention that the materials are much more stable to water than previously employed systems such as polyurethanes.

In a preferred continuous process the prepolymer mixture in liquid form is coated on to a length of flexible fabric by means of a blade over flat bed and the coated fabric dried, if necessary. The coated fabric can then be split into suitable size strips and rolled up into bandages.

The amount of prepolymer on the fabric carrier should be sufficient to ensure that the resultant cast has adequate strength. Suitable amounts have been found to be 50 to 500 g/m$^2$, preferably 100 to 350 g/m$^2$, for example 200 g/m$^2$, 250 g/m$^2$ or 300 g/m$^2$.

Preferably, the bandages should be protected during storage from water and excessive moisture vapour to prevent a premature setting taking place, the bandages can be conventionally packaged in heat sealed waterproof pouches such as metal foil polyethylene laminate or polyethylene pouches. Again it is one of the considerable advantages of this invention that it is possible to use simple procedures and packages such as using polyethylene pouches.

In use the bandages may be brought into contact with water and wrapped around the injured part of the body. The setting bandage has a working time which is a time sufficient to allow the bandage to be positioned, and a set time which is the time taken for the cast to become rigid. Favoured working times are 1 minute to 6 minutes and especially 2 minutes to 4 minutes. Favoured set times are 5 minutes to 30 minutes and especially 6 minutes to 15 minutes.

Conventional orthopaedic bandages are soaked in water prior to application. It has now been discovered that orthopaedic bandages which employ hydrophilic prepolymers as described and a water-activated vinyl polymerisation catalyst in order to set can also be employed in an alternative and preferred mode, namely the bandage may be applied dry and then set off in situ by introducing water to the bandage which water may optionally contain further component of a multicomponent catalyst as necessary.

Accordingly, the present invention provides a method of forming a splint which method comprises positioning a splinting bandage about the member to be immobilised said splinting bandage being adapted to set by polymerisation of vinylic groups on introduction of water and thereafter causing the bandage to set by introducing water to the bandage.

Therefore, the present invention still further provides a method of forming a rigid orthopaedic cast for body members which comprises providing an orthopaedic bandage comprising a support carrying a vinyl compound which polymerises when exposed to a water-activated vinyl polymerisation catalyst; providing a water-activatable vinyl polymerisation catalyst; activating the catalyst by bringing it into contact with water; exposing the vinyl compound to the activated catalyst; and wrapping the orthopaedic bandage around the member to be immobilised, characterised in that the vinyl compound is a prepolymer which contains not less than two polymerisable vinyl groups.

Preferably the orthopaedic bandage is wrapped around the member to be immobilised before the catalyst is brought into contact with the water.

Suitably the water is sprayed or sponged on to the bandage, for example by using a spray or a sponge or cloth.

The water may contain a wetting agent such as a surfactant or a lower alkanol such as isopropanol but it is preferred to use water without adding such agents.

It is one of the considerable advantages of this invention that a cast may be produced by wetting the bandage once it has been positioned on the body. It is a further considerable advantage that the setting-off of the bandage may be accomplished by treatment with such a non-toxic agent as water.

For this aspect of the invention it has been found that it is advantageous that the bandage be sufficiently tacky to adhere to itself in the dry state so that moulding around a limb or other part of the body is simplified. It is one of the advantages of using a tacky prepolymer that such tacky bandages may be obtained. Thus favoured prepolymers for use in this invention are non-solid prepolymers (that is preferably viscous liquid prepolymers) since such prepolymers) since such prepolymers are more tacky than solid prepolymers.

The following Examples (except nos. 14, 28, 29, 32). illustrate the invention.

EXAMPLE 1

Preparation of Prepolymer

To a well stirred mixture of Desmodur N (329.7 g 1.74 mol —NCO, Bayer) and dibutyl tin dilaurate (1.1 g, BDH) a mixture of 2-hydroxyethyl methacrylate (181 g, total —OH 1.48 mol), PEG 6000 (66.8 g, total —OH 0.087 mol), N,N-dimethylethanolamine (14.69 g, 0.174 mol total —OH) and pheothiazine (0.3 g) was added dropwise over 1 hour. The reaction is exothermic and should be cooled in a water bath so that pot temperature does not exceed 60° to 70° C. Gas is evolved from the reaction between isocyanate and water from the added reagents.

The reaction mixture is then heated with stirring to 70° C. for ½ hour and allowed to cool. Dry dichloromethane (200 ml) and Tinuven P (3 g, Ciba Geigy) are added and the mixture is stirred until homogenous the poured into a bottle and capped.

Spreading a Bandage

To spread a bandage the following mixture is made up: 30 g resin/$CH_2Cl_2$ mixture, 10 g alumina powder, 0.9 g catalyst (a finely ground mixture of 1 part CU(AcAc)$_2$ to 50 parts sodium metabisulphite), 0.9 g Sylosiv A4 (W. R. Grace & Co.) and 6 ml dichloromethane.

The mixture is evenly spread onto polyester net (Steibel of Nottingham B522) 2½ m×8 cm and then dried with warm, dry air. The bandage is then rolled onto a former and stored in a sealed bag.

Application of the bandage

The bandage is applied dry and is then treated with an activating spray (water plus a suitable wetting agent such as IPA, ethanol or detergent) whereupon it sets.

EXAMPLE 2

Preparation of the Hydrophilic prepolymer

The required amounts of Desmodur N100, (1.2 mol NCO), 2-hydroxymethyl methacrylate (0.8 mol) and polyethylene glycol monomethacrylate (0.4 mol OH) were weighed into a wide neck jar. The reaction mixture was hand mixed until a clear solution was obtained (approximately 1 minute). Dibutyl tin dilaurate catalyst was added to increase the reaction rate and the reaction allowed to continue with mixing until the reaction exotherm had subsided. (Approximately 5 to 10 minutes). The prepared prepolymer was then stored in the dark for approximately 24 hours.

Preparation of an Orthopaedic Bandage

The hydrophilic prepolymer of Example 2 containing 500 ppm of phenothiazine polymerisation inhibitor was mixed with a catalyst composition (2% by weight of the prepolymer) consisting of 1 part by weight of cupric acetylacetonate and 50 parts by weight of sodium metabisulphate and alumina filler (20% by weight of grade G5238).

The prepolymer liquid mixture was coated onto a warp knitted polyester substrate (10 cm×1 meter) to give a coating weight per unit area of approximately 150 g/m$^2$ to form the orthopaedic bandage of the invention. The bandage strip was wound onto a core to form a roll and packed in a polythene pouch.

The bandage was made into a cast by immersing the bandage roll in water and wrapping the unrolled bandage around a 2.5 cm spindle. The bandage had a working time of 2 minutes and a set time of 15 minutes.

EXAMPLE 3

Preparation of Prepolymer

A mixture of an aliphatic isocyanate (384.6 g, Desmodur N 100), dibutyl tin dilaurate (1.4 g) and dry dichloromethane (210 ml) was warmed with stirring until the mixture was refluxing gently. To this mixture was added dropwise over 1 hour a mixture of 2-hydroxyethyl methacrylate (211.4 g), polyethylene glycol (77.9 g, molecular weight 6000, Breox PEG 8000), N,N-dimethylethanolamine (17.1 g) phenothiazine (0.3 g) and dry dichloromethane (210 ml). The reaction mixture was maintained at reflux temperature and stirred during the addition. The final mixture was heated to reflux temperature and stirred for a further hour. Tinuven P (3.4 g) was then added and the mixture stirred until homogenous. The mixture was then allowed to cool and poured into a glass jar and firmly stoppered.

Preparation of an Orthopaedic Bandage

A mixture of the resin as prepared above (38 g), alumina powder (10 g), catalyst (0.9 g) (a finely ground mixture of 1 part copper (II) acetyl acetonate to 50 parts sodium metabisulphate), Sylosiv A4 (0.9 g) was prepared. This mixture was spread evenly onto polyester net (20 cm×4 m at about 100 gsm) and this was then dried with warm dry air. This bandage was then rolled onto a former and stored in a sealed bag.

EXAMPLES 4–24

Prepolymers were prepared using the method described in Example 3 but in which various components were changed on an equivalent mole for mole basis.

| Example | Isocyanate type | Vinyl Compound | | Accelerator |
|---|---|---|---|---|
| | | | Polyoxyalkylene glycol | |
| 4 | Desmodur N 100 | Hydroxyethyl acrylate | PEG 6000 | N,N—dimethyl ethanolamine |
| 5 | Desmodur N 100 | Hydroxypropyl acrylate | PEG 6000 | N,N—dimethyl ethanolamine |
| 6 | Desmodur N 100 | Glycerol monomethyl-ether mono-methacrylate | PEG 6000 | N,N—dimethyl ethanolamine |
| 7 | Desmodur N 100 | Diallylamine | PEG 6000 | N,N—dimethyl ethanolamine |
| 8 | Desmodur R | Hydroxyethyl methacrylate | PEG 6000 | N,N—dimethyl ethanolamine |
| | | | Polyoxyalkalene Glycol | |
| 9 | Desmodur L | Hydroxyethyl methacrylate | PEG 6000 | N,N—dimethyl ethanolamine |
| 10 | PAPI 135 | Hydroxyethyl methacrylate | PEG 6000 | N,N—dimethyl ethanolamine |
| 11 | Desmodur W | Hydroxyethyl methacrylate | PEG 6000 | N,N—dimethyl ethanolamine |
| 12 | Desmodur N100 | Hydroxyethyl methacrylate | PEG 6000 | N,N—dimethyl ethanolamine |
| 13 | Desmodur N100 | Hydroxyethyl methacrylate | PEG 1500 | N,N—dimethyl ethanolamine |
| 14 | Desmodur N100 | Hydroxyethyl methacrylate | Polypropylene glycol 1025 | N,N—dimethyl ethanolamine |
| 15 | Desmodur N100 | Hydroxyethyl methacrylate | Pluronic L35 | N,N—dimethyl ethanolamine |
| 16 | Desmodur N100 | Hydroxyethyl methacrylate | Pluronic L64 | N,N—dimethyl ethanolamine |
| 17 | Desmodur N100 | Hydroxyethyl methacrylate | PEG 6000 | N,N—diethyl ethanolamine |
| 18 | Desmodur N100 | Hydroxyethyl methacrylate | PEG 6000 | N—methyl piperidin-2-methanol |
| 19 | Desmodur N100 | Hydroxyethyl methacrylate | PEG 6000 | N—methyl, N—2-hydroxyethyl analine |
| 20 | Desmodur N100 | Hydroxyethyl methacrylate | PEG monomethyl ether 1900 | N,N—dimethyl ethanolamine |
| 21 | MDI | Hydroxyethyl methacrylate | PEG 6000 | N,N—dimethyl ethanolamine |
| 22 | Desmodur N100 | Hydroxyethyl Methacrylate | Breox 75W/270 | N,N—dimethyl ethanolamine |
| 23 | Desmodur N100 | Hydroxyethyl methacrylate | Breox 75W/18000 | N,N—dimethyl ethanolamine |
| 24 | Isonate 143L | Hydroxyethyl methacrylate | PEG 6000 | N,N—dimethyl ethanolamine |

PEG 6000 used is Breox 8000
Pluronic L64 is a polyoxyethylene-polyoxypropylene diol block copolymer of molecular weight 2900
Pluronic L35 has a molecular weight of 1900
Desmodur N100 is an aliphatic isocyanate of functionality 3.
Desmodur W is an alicyclic isocyanate of functionality 2 MDI is 4'4 diphenylmethane di-isocyanate
Breox 75W 270 and Breox 75W 1800 are PEG/PPG copolymers available from British Petroleum.
Isocyanate 143L is a modified MDI which is liquid at room temperature, available from Upjohn.
Desmodur L and R are aromatic isocyanates of functionality
3. Desmodur isocyanates are available from Bayer. Tween 80 is a polyethoxylated sorbitan monolaurate of molecular weight 3800, PEG 1500 is polyethylene glycol molecular weight 1500 available from British Petroleum.
PAPI is phosgenated analine formaldehyde condensate isocyanate available from Upjohn.

Application of the Bandage

The bandage may be applied to the appropriate limb dry and then treated with an activating spray (water with a suitable wetting agent such as isopropyl alcohol, ethanol or a surface active agent). The bandage then sets to form a supporting bandage around the limb.

EXAMPLES 25–31

Prepolymers (except Examples 28 and 29) were prepared using the method described in Example 3 but in which various components were changed as follows. Examples 28 and 29 were prepared by the reaction of the glycol with two moles of acryloyl chloride.

| | | |
|---|---|---|
| 25. Desmodur N100 | 1 mole NCO | |
| Hydroxyethyl methacrylate | .88 mole OH | |
| PEG 6000 | .05 mole OH | |
| 3-N,N—diethylamino-2-hydroxypropyl methacrylate | .1 mole OH | |
| 26. Desmodur N100 | 1 mole NCO | |
| Hydroxyethyl methacrylate | .9 mole OH | |
| 2-Hydroxy-3-methacryloxy propyl trimethyl ammonium chloride | .1 mole OH | |
| 27. Desmodur N100 | 1 mole NCO | |
| Hydroxyethyl methacrylate | .7 mole OH | |
| PEG 1500 | .1 mole OH | |
| Methyl diethanolamine | .2 mole OH | |
| 28. PEG 1500 dimethacrylate | | |
| 29. PEG 300 dimethacrylate | | |
| 30. Isonate 143L | 1 mole NCO | |
| Hydroxyethyl methacrylate | .79 mole OH | |
| Tween 80 | .11 mole OH | |
| N,N—dimethyl ethanolamine | .1 mole OH | |
| 31. Isonate 143L | 1 mole NCO | |
| Hydroxyethyl methacrylate | .8 mole OH | |
| Ethoxylated glycerol mw 1256 | .1 mole OH | |
| N,N—dimethyl ethanolamine | .1 mole OH | |

EXAMPLE 32 (NOT ILLUSTRATIVE OF INVENTION)

Preparation of Resin 4,4'-Isopropylidine diphenol (87 g) was added to glycidyl methacrylate (150 g) and hydroquinone (0.02 g). The temperature of the mixture was raised to 60° C. under an atmosphere of dry nitrogen gas and stirred until the solution was clear of all solid particles. Dimethyl-p-toluidine (2.0 g) was added and the reaction flask covered with aluminium foil to keep out the light. When the reaction was complete the product was purified to remove excess glycidyl methacrylate by chromatography.

Preparation of Bandage

The purified bisphenol-A-glycidyl methacrylate adduct was mixed with alumina powder and catalyst (a finely ground mixture of 1 part copper acetyl acetonate and 50 parts sodium metabisulphite) and spread onto a polyester net at a weight of 100 gsm.

EXAMPLES 33 TO 38

Preparation of Hydrophilic Prepolymers

The aliphatic isocyanate (Desmodur N100), 2-hydroxymethyl methacrylate and/or polyethylene glycol monomethacrylate (PE 350 or Sipomer PEG MM) in the required amounts were weighed into a wide neck jar. The reaction mixture was hand mixed until a clear solution was obtained (approximately 1 minute). Dibutyl tin dilaurate catalyst was added to increase the reaction rate and the reaction allowed to continue with mixing until the reaction exotherm had subsided. (Approximately 5 to 10 minutes). The prepared prepolymer was then stored in the dark for approximately 24 hours.

Prepolymers were prepared according to the method given above.

| Example No. | Desmodur N100 (moles) | 2-HEMA (moles) | PE 350 (moles) | Sipomer PEG MM (moles) | Catalyst (g) |
|---|---|---|---|---|---|
| 33 | 0.1 | 0.30 | — | — | 0.15 |
| 34 | 0.05 | — | 0.15 | — | 0.19 |
| 35 | 0.05 | 0.10 | 0.05 | — | 0.12 |
| 36 | 0.05 | 0.075 | 0.075 | — | 0.13 |
| 37 | 0.10 | 0.20 | — | 0.10 | 0.20 |
| 38 | 0.40 | 0.80 | — | 0.40 | 0.80 |

EXAMPLES 39 TO 43

The following Examples demonstrate the setting rate of prepolymers (3 g) of Examples 33, 34, 35 and 36 when hand mixed in a tube with a redox catalyst (cupric acetonylacetonate-sodium metabisulphite mixture in a 1:50 weight ratio) and water (20% by weight of the prepolymer). The time was recorded when hand mixed sample of the setting prepolymer mixture formed a gel. The gel and set times of the setting prepolymer mixture was also determined on a setting rheometer.

| Example No. | Prepolymer | Catalyst % by wt. | Hand Mix Gel (mins) | Rheometer Gel (mins) | Rheometer Set (mins) |
|---|---|---|---|---|---|
| 39 | Ex. 33 | 1 | 1.8 | 2.2 | 13 |
| 40 | Ex. 33 | 2 | 0.9 | 1.2 | 10 |
| 41 | Ex. 34 | 0.5 | 0.2 | rapid reaction | |
| 42 | Ex. 35 | 0.5 | 0.6 | 1.8 | 10 |
| 43 | Ex. 36 | 0.5 | 0.2 | rapid reaction | |

EXAMPLES 44 TO 50

Examples 44 to 50 were prepared in the same manner as Examples 39 to 43 using the prepolymer of Example 38 mixed with different proportions (0.1 to 1.0% by weight of the prepolymer) of a redox catalyst consisting of sodium sulphite (SS) and cupric acetonyl acetonate (CuAc) in various ratios (1:1 to 1000:1).

The hand mix gel and the rheometer gel and setting times were determined in the same manner as Examples 30 to 43.

| Example No. | Ratio of SS/CuAc | Catalyst % by wt. | Hand Mix Gel (mins) | Rheometer Gel (mins) | Rheometer Set (mins) |
|---|---|---|---|---|---|
| 44 | 1000:1 | 1.0 | 0.9 | 3.0 | >15 |
| 45 | 100:1 | 1.0 | 0.6 | 1.8 | 10 |
| 46 | 1:1 | 1.0 | 0.6 | 1.1 | 9.0 |
| 47 | 1:1 | 0.5 | 0.75 | 1.3 | 7.0 |
| 48 | 1:1 | 0.5 | 0.5 | 1.0 | 8.0 |
| 49 | 1:1 | 0.3 | 1.5 | 2.0 | 9.0 |
| 50 | 1:1 | 0.1 | — | 7.1 | >15 |

SS — Sodium sulphite CuAc — Cupric aceonyl acetonate

EXAMPLES 51 TO 54

Examples 51 to 54 were prepared in the same manner as Example 48 containing different proportions of a polymerisation inhibitor (0 to 750 ppm of methoxyhydroquinone). The hand mixed gel and the rheometer gel and setting times were determined in the same manner as that of Examples 39 to 43.

|  |  |  | Rheometer | |
|---|---|---|---|---|
| Example No. | MEHQ (ppm) | Hand Mix Gel (mins) | Gel (mins) | Set (mins) |
| 51 | — | 0.5 | 1.0 | 8.0 |
| 52 | 250 | 0.75 | 1.0 | 7.0 |
| 53 | 500 | 0.75 | 1.0 | 8.0 |
| 54 | 750 | 0.75 | 1.0 | 12.0 |

Similar setting rates were obtained with prepolymer mixtures containing phenothiazine as the polymerisation inhibitor in place of methoxy hydroquinone (MEHQ).

EXAMPLES 55 TO 71

Examples 55 to 71 were prepared in the same manner as Examples 39 to 43 using the prepolymer of Example 38 mixed with different proportions (1 to 10% by weight) of different redox catalyst systems. The hand mixed gel and rheometer gel and setting times were determined in the same manner as Examples 39 to 43.

|  |  |  | Hand Mix | Rheometer | |
|---|---|---|---|---|---|
| Example No. | Redox Catalysts | Catalyst % by wt. | Gel (mins) | Gel (mins) | Set (mins) |
| 55 | SS | 3.0 | 1.5 | — | — |
| 56 | SS/PP 1:3 | 2.0 | 2.5 | — | — |
| 57 | SS/PP 1:3 | 2.0 | 2.0 | >5 | — |
| 58 | SS/PP 1:3 | 3.0 | 1.5 | 2.5 | >15 |
| 59 | SS/PP 1:3 | 4.0 | 1.5 | 3.0 | >15 |
| 60 | SS/PP 1:3 | 5.0 | 1.0 | 2.0 | 12 |
| 61 | SS/PP 3:1 | 5.0 | 1.5 | 3.0 | >15 |
| 62 | ST/PP 1:3 | 5.0 | — | — | — |
| 63 | ST/PP 1:3 | 10.0 | 3.0 | 4.9 | >15 |
| 64 | SS + 10 ppm CS | 3.0 | 0.5 | 1.0 | 6.5 |
| 65 | ST + 10 ppm CS | 3.0 | — | — | — |
| 66 | PP + 10 ppm CS | 3.0 | — | — | — |
| 67 | ST/PP 1:3 + 10 ppm CS | 1.0 | 2.5 | 4 | >15 |
| 68 | ST/PP 1:3 + 10 ppm CS | 2.0 | 0.6 | 0.9 | 7.5 |
| 69 | ST/PP 1:3 + 10 ppm CS | 5.0 | 0.6 | 0.9 | 6.0 |
| 70 | ST/PP 1:3 + 3 ppm CS | 2.0 | 0.5 | 0.9 | 7.5 |
| 71 | ST/PP 1:3 + 3 ppm CS | 5.0 | 1.7 | 2.2 | 8.0 |

SS — sodium sulphite
PP — potassium persulphate
ST — sodium thiosulphate
CS — copper sulphate (CuSO$_4$ 5H$_2$O) was added in amounts expressed as parts per million of the prepolymer (ppm).

EXAMPLE 72

Preparation of an orthopaedic bandage

The hydrophilic prepolymer of Example 38 containing 500 ppm of phenothiazine polymerisation inhibitor was mixed with a catalyst composition (2% by weight of the prepolymer) consisting of 1 part by weight of cupric acetylacetonate and 50 parts by weight of sodium metabisulphate and alumina filler (20% by weight of grade G5438).

The prepolymer liquid mixture was coated onto a warp knitted polyester substrate (10 cm × 1 meter) to give a coating weight per unit area of approximately 150 g/m$^3$ to form the orthopaedic bandage of the invention. The bandage strip was wound onto a core to form a roll and packed in a polyethylene pouch.

The bandage was made into a cast by immersing the bandage roll in water and wrapping the unrolled bandage around a 2.5 cm spindle. The bandage had a working time of 2 minutes and a set time of 15 minutes.

Application of Bandage

The bandage as prepared above is applied dry and is treated with an activating spray of water. The resin provides an adequate cast as measured above.

EXAMPLE 73

The prepolymers formed in Examples 1 to 32 were mixed with alumina and catalyst and spread onto a polyester net as described in Example 3. The cast forming of the prepolymers was assessed by wrapping the prepolymer coated net around a former to make a cylinder. The former was removed and the cylinder wall clamped in an Instron Testing Machine so as to measure diametral compression and extension forces. The machine was adapted so that the moving clamp would oscillated between positions 0.6 mm from the rest position. The force required to deform the cast as it set over a period of time was measured. The prepolymer covered net was therefore positioned in the jaws of the machine and then sprayed with water and the jaws caused to oscillate. The increasing force required to deform the cast as it set was recorded on a chart recorder. From the results it was possible to see that a poor cast forming material required only a small force to cause deformation even after a prolonged time. A fair cast required a large force to cause deformation but this value was only reached after a period of at least one hour. A good cast required a large force to cause deformation and this was achieved after a short period, less than 20 minutes.

| Example | |
|---|---|
| 1 | Very good |
| 2 | Good |
| 3 | Very good |
| 4 | Very good |
| 5 | Very good |
| 6 | Very good |
| 7 | Poor |
| 8 | Very good |
| 9 | Very good |
| 10 | Very good |
| 11 | Good |
| 12 | Good |
| 13 | Very good |

23

-continued

| Example | |
|---|---|
| 14 | Fair |
| 15 | Good |
| 16 | Good |
| 17 | Good |
| 18 | Good |
| 19 | Fair |
| 20 | Good |
| 21 | Very good |
| 22 | Good |
| 23 | Good |
| 24 | Very good |
| 25 | Fair |
| 26 | Fair |
| 27 | Good |
| 28 | Good |
| 29 | Fair |
| 30 | Very good |
| 31 | Very good |
| 32 | Failed |

EXAMPLE 74

Preparation of Cast (a) Preparation of Prepolymer

Using the method of preparing prepolymer described in Example 3, a prepolymer was prepared of the following composition: Desmodur N100 (1 mole NCO), hydroxyethylmethacrylate (0.8 mole OH), PEG 1500 (0.1 mole OH) and dimethylethanolamine (0.1 mole OH).

(b) Preparation of Compositions

Prepolymer (19 g, including solvent) and copper (II) acetyl acetonate (0.9% w/v in methylene chloride solution, 0.5 ml) were mixed until homogeneous. Sodium metabisulphite (0.45 g) and molecular sieve A4 (0.45 g) were mixed in until homogeneous. Sodium aluminosilicate (Zeolex 323, 7 g) was mixed in until homogeneous to yield the composition for spreading. A second composition was prepared in the same manner except that tartaric acid (0.05 g) was mixed in prior to the addition of the sodium aluminosilicate.

(c) Preparation of Bandage

The composition was spread onto the support by hand using a neoprene squeegee to a weight per unit area of approximately 250 gm$^{-2}$ and dried in a warm air current (weight of dried composition).

The support was a Raschel warp knit polyester fabric 10 cm wide with a weight per unit area of about 110 gm$^{-2}$. A second bandage was prepared in the same manner employing the second composition.

(d) Preparation of Casts

The forearm of a volunteer was wrapped with a layer of fleece. The bandage was then wrapped around the forearm over the fleece to give five layers of bandage. The bandage was sprayed with water until thoroughly wetted. After 20 minutes a rigid cast had formed. The cast was removed (cut off) and the second bandage used to form a cast in the same manner. Although both casts had the same initial properties the cast made from the tartaric acid containing composition maintained its creamy white appearance whereas the cast which did not contain the tartaric acid darkened in colour after a few days.

EXAMPLE 75

Preparation of Bandages

A series of bandages were prepared by the method of Example 3. The prepolymers were the same except that the amount of PEG 6000 was varied (with corresponding variations in the amount of hydroxyethylmethacrylate) as follows: 0, 0.025, 0.05, 0.1, 0.15, 0.2, 0.25 (mole OH). The levels of PEG 6000 which gave the fastest rate of strength build up after spraying was 0.05 (mole OH). A further series of bandages were made in analogous manner but in which the amount of dimethylethanolamine was varied as follows: 0, 0.05, 0.1, 0.15, 0.2, 0.25 (mole OH). The level of DMEA which gave fastest rate of strength build up after spraying was 0.1 (mole OH). Yet another series of bandages were made in which the PEG 6000 was replaced by an equivalent amount (molar basis) of PEG 1500. The level of PEG 1500 which produced the fastest rate of strength build up after spraying was found to occur with 0.1 mole of PEG 1500. The bandages containing PEG 1500 maintained their unrolling properties on storage better than those containing PEG 6000.

We claim:

1. An orthopaedic bandage which comprises a support carrying a vinyl compound, which compound polymerises when exposed to a water-activated vinyl polymerisation catalyst, in which the vinyl compound is a hydrophilic prepolymer which contains not less than two polymerisable vinyl groups said prepolymer comprising (a) a vinylic component of the formula:

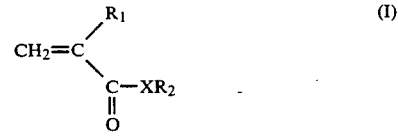

wherein $R_1$ is hydrogen or methyl; X is O or NH and $R_2$ is selected from the group consisting of hydroxyalkyl, hydroxyaryl, aminoalkyl, aminoaryl and aminoaryl substituted at the nitrogen by alkyl;

(b) a hydrophilic components selected from the group consisting of a polyoxyalklated vinyl compound and a compound containing a moiety of the formula:

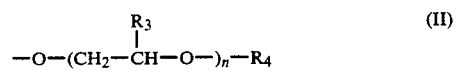

wherein n is 10 to 255; $R_3$ is hydrogen or methyl; $R_4$ is a bond, hydrogen or lower alkyl and $R_3$ is the same or different in adjacent repeat units with the proviso that at least 50% of the units, $R_3$ is hydrogen and (c) a polyfunctional organic compound capable of forming ester, ether, amide or urethane linkages with the components of (a) and (b).

2. A bandage according to claim 1 in which the polymerisable vinyl groups are acrylate or methacrylate groups and the prepolymer is mixed with a water activated acrylic polymerisation catalyst.

3. A bandage according to claim 1 in which the prepolymer contains not less than three acrylic ester or methacrylic ester groups and said prepolymer is a viscous liquid.

4. A bandage according to claim 1 in which the prepolymer is water swellable to the extent of being able to absorb at least 10% by weight of its own weight of water.

5. A bandage according to claim 1 in which the prepolymer is dispersible in water.

6. A bandage according to claim 1 in which the prepolymer contains a tertiary amino group.

7. A bandage according to claim 6 in which the tertiary amino group is a dimethylaminoethyl group.

8. A bandage according to claim 1 in which the prepolymer contains 6 to 40% by weight of polyethylene oxide.

9. A bandage according to claim 2 in which the prepolymer contains acryloyloxy lower alkoxy or methacryloyloxy lower alkoxy groups.

10. A bandage according to claim 9 in which the prepolymer contains methacryloyloxyethyloxy groups.

11. A bandage according to claim 2 in which the polyfunctional organic compound forms a urethane linkage and comprises an aliphatic isocyanate functionality of not less than 2.

12. A bandage according to claim 11 in which the isocyanate has a functionality of 3.

13. A bandage according to claim 2 in which the prepolymer has an average molecular weight in the range of 1100 to 16,000.

14. A bandage according to claim 2 in which the catalyst comprises a copper (II) compound and a reducing agent.

15. A bandage according to claim 14 in which the reducing agent is sodium metabisulphite.

16. A bandage according to claim 15 in which the copper compound is copper (II) acetyl acetonate.

17. A bandage according to claim 14 in which the bandage additionally contains a polybasic organic acid.

18. A bandage according to claim 17 wherein the acid is tartaric acid.

19. A process for the preparation of an orthopaedic bandage according to claim 1 which process comprises coating or impregnating a support with a hydrophilic prepolymer of claim 1 which polymerises when exposed to a water-activated polymerisation catalyst, the catalyst or at least one component thereof being uniformly dispersed in the hydrophilic prepolymer.

* * * * *